United States Patent [19]

Lepage et al.

[11] Patent Number: 5,464,860
[45] Date of Patent: Nov. 7, 1995

[54] N(PYRAZOL-3-YL) BENZAMIDES AND PHARMACEUTICAL COMPOSITIONS

[75] Inventors: Francis Lepage, Creteil; Bernard Hublot, Paris, both of France

[73] Assignee: Novapharme, Paris, France

[21] Appl. No.: 77,194

[22] Filed: Jun. 16, 1993

Related U.S. Application Data

[63] Continuation-in-part of Ser. No. 697,607, May 9, 1991, Pat. No. 5,258,397.

Foreign Application Priority Data

Nov. 30, 1988 [FR] France .................. 88 15718
May 30, 1990 [FR] France .................. 90 06735

[51] Int. Cl.⁶ .................. A61K 31/415; C07D 231/40
[52] U.S. Cl. .................. 514/404; 548/368.4; 548/372.5
[58] Field of Search .................. 548/368.4, 372.5; 514/404

[56] References Cited

U.S. PATENT DOCUMENTS

| | | |
|---|---|---|
| 3,905,997 | 9/1975 | Zinnes et al. . |
| 4,416,683 | 11/1983 | Burow, Jr. .................. 548/372.5 |
| 5,001,124 | 3/1991 | Patterson et al. . |
| 5,086,184 | 2/1992 | Burow, Jr. . |

FOREIGN PATENT DOCUMENTS

| | | |
|---|---|---|
| 0508225 | 7/1978 | Australia . |
| 0029363 | 5/1981 | European Pat. Off. . |
| 0049071 | 4/1982 | European Pat. Off. . |
| 0065723 | 12/1982 | European Pat. Off. . |
| 0276177 | 7/1988 | European Pat. Off. . |
| 2313046 | 6/1976 | France . |
| 2337997 | 1/1977 | France . |
| 0371876 | 6/1990 | France . |

OTHER PUBLICATIONS

Chemical Abstracts, vol. 84, No. 23, Jun. 7, 1976:164767r, p. 468.
Chemical Abstracts, vol. 87, No. 19, Nov. 7, 1977: 152174u, p. 593.

*Primary Examiner*—Robert W. Ramsuer
*Attorney, Agent, or Firm*—Jacobson, Price, Holman & Stern

[57] ABSTRACT

The invention relates to a compound useful for treating epilepsy selected from the compounds of the general formula:

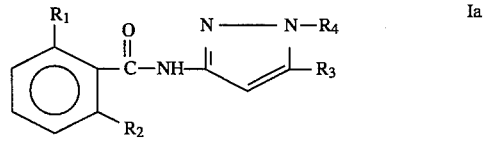

in which
$R_1$ is $C_1$–$C_4$ alkyl,
$R_2$ is $C_1$–$C_4$ alkyl,
$R_3$ is selected from hydrogen, $C_1$–$C_4$ alkyl, $C_1$–$C_4$ alkoxy and $C_1$–$C_4$ hydroxyalkyl, and
$R_4$ is selected from hydrogen, $C_1$–$C_4$ alkyl, $C_2$–$C_7$ alkanoyl and $C_1$–$C_4$ hydroxyalkyl.

10 Claims, No Drawings

N(PYRAZOL-3-YL) BENZAMIDES AND PHARMACEUTICAL COMPOSITIONS

This application is a CIP of application Ser. No. 07/697,607, filed on May 9, 1991, now U.S. Pat. No. 5,258,347.

The present invention relates in a general manner to novel heterocyclic derivatives endowed with anticonvulsant activity, a process for their preparation as well as to therapeutic compositions containing them.

A relatively small number of agents with anticonvulsant activity are available. A large number of them possess disadvantages associated with therapeutic escape phenomena, troublesome side effects such as diminution of vigilance, drowsiness, . . . or toxic, in particular hepatotoxic, effects.

The aim of the present invention is to provide novel compounds with anticonvulsant properties and free from the disadvantages of the prior art.

Thus the object of the present invention is heterocyclic compounds of general formula:

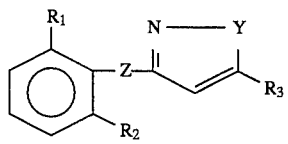

in which

Y is selected from

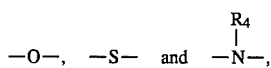

$R_4$ being selected from hydrogen, $C_1$–$C_4$ alkyl, benzyl, halogenobenzyl, $C_2$–$C_7$ acyl and $C_1$–$C_4$ alkyl substituted by a $C_2$–$C_7$ alkanoyloxy, $C_1$–$C_4$ dialkylamino, $C_1$–$C_4$ alkoxy, phenoxy or halogenophenoxy group, Z is selected from the groups —$CON(R_6)$—, —NH—CO—CH=CH— and —$N(R_6)$—CO— in which $R_6$ is selected from hydrogen and $C_1$–$C_4$ alkyl, $R_1$ is $C_1$–$C_4$ alkyl, $R_2$ is selected from $C_1$–$C_4$ alkyl and halogen, $R_3$ is selected from hydrogen, $C_1$–$C_4$ alkyl, $C_1$–$C_4$ alkoxy, $C_1$–$C_4$ hydroxyalkyl, $C_1$–$C_4$ halogenoalkyl, $C_2$–$C_7$ alkanoyl and a —$CHR_{10}OR_5$ group in which $R_5$ is selected from $C_1$–$C_4$ alkyl, an unsubstituted phenyl or phenyl substituted by one or more substituents selected from halogen, $C_1$–$C_4$ alkyl, $C_1$–$C_4$ alkoxy and trifluoromethyl; and a $COR_7$ group, $R_7$ being selected from $C_1$–$C_4$ alkyl, phenyl and a

group, $R_8$ and $R_9$ being selected from hydrogen and $C_1$–$C_4$ alkyl and $R_{10}$ represents hydrogen or $C_1$–$C_4$ alkyl.

The compounds of formula (I) comprise in particular the compounds in which the heterocycle is a pyrazole, i.e. Y represents the —$NR_4$— group, in which $R_4$ is preferably selected from hydrogen, methyl, acetyl and methoxyethyl.

Other compounds of formula I are those in which the heterocycle is an isoxazole (Y is O), the preferred derivatives in this case being those in which $R_3$ represents hydroxyalkyl, halogenoalkyl, alkyl or acetyl.

The preferred compounds of the latter, are those in which Z represents a —CO—$N(R_6)$—group, $R_6$ preferably denoting hydrogen or methyl.

Other preferred compounds of formula I are also those in which $R_1$ represents methyl, $R_2$ represents chlorine, methyl or isopropyl, $R_3$ represents methyl or methoxy when the heterocycle is pyrazole and the —$CH_2OR_5$ group in which $R_5$ is methyl, phenyl or phenyl substituted by halogen such as fluorine or bromine, trifluoromethyl or two methoxy groups when the heterocycle is an isoxazole.

More specifically the present invention relates to a compound selected from the compounds of the general formula:

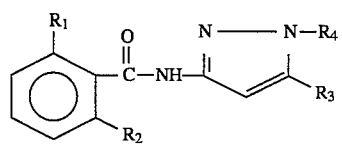

in which $R_1$ is $C_1$–$C_4$ alkyl, $R_2$ is $C_1$–$C_4$ alkyl, $R_3$ is selected from hydrogen, $C_1$–$C_4$ alkyl, $C_1$–$C_4$ alkoxy and $C_1$–$C_4$ hydroxyalkyl, and $R_4$ is selected from hydrogen, $C_1$–$C_4$ alkyl, $C_2$–$C_7$ alkanoyl and $C_1$–$C_4$ hydroxyalkyl.

Of the preferred compounds according to the invention more particular mention may be made of:

3-(2-chloro 6-methyl phenylcarbamoyl) 1-acetyl 5-methyl pyrazole,

N-(1,5-dimethyl-3-pyrazolyl)2,6-dimethylbenzamide, 3-(2,6-dimethyl phenylcarbamoyl) 1,5-dimethylbenzamide, 3-(2-chloro 6-methyl phenylcarbamoyl) 1,5-dimethylpyrazole, 3-(2,6-dimethyl phenylcarbamoyl) 1-methyl 5-methoxy pyrazole, and 3-(2,6-dimethyl phenylcarbamoyl) 5-fluoromethyl isoxazole.

The present invention also relates to a process for the preparation of the compounds of general formula I, wherein a compound of general formula:

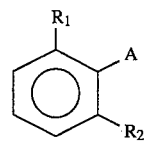

in which $R_1$ and $R_2$ have the same meanings as in formula I and A represents a —COOH, —COCl or —$N(R_6)$H group in which $R_6$ represents hydrogen or $C_1$–$C_4$ alkyl is reacted with the compound of general formula:

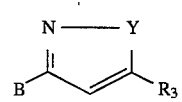

in which Y and $R_3$ have the same meanings as in formula I and B represents a —COOH, —COCl, —CH=CH—COOH, —CH=CH—COCl or —$N(R_6)$H group, $R_6$ being H or $C_1$–$C_4$ alkyl. In particular, a) When Z represents the groups —$N(R_6)$—CO— or —NH—CO—CH=CH—, $R_6$ being as defined in the general formula I, an amine of general formula II in which A represents the —$NR_6$H group is condensed with an acid or an acid chloride of general formula III in which B represents a —COOH, —COCl, —CH=CH—COOH or —CH=CH—COCl.

When an acid of general formula III is used, the reaction is carried out in the presence of dicyclohexylcarbodiimide (DCC) or carbonyldiimidazole (CDI) in a solvent which may be dimethylformamide (DMF) or tetrahydrofuran (THF) at a temperature between 10° and 25° C.

In the case in which an acid chloride (III) is used, the condensation is carried out in the presence of a proton acceptor such as triethylamine or potassium carbonate at a temperature between 20° and 120° C. in a neutral solvent such as toluene, acetone, etc.

The acids of general formula III (Y=—NR$_4$—) are known from the literature.

These are, in particular, the acids:
1-methyl 5-methoxy pyrazole 3-carboxylic acid
3-(1,5-dimethyl pyrazolyl) acrylic acid
1,5-dimethyl pyrazole 3-carboxylic acid
5-methyl pyrazole 3-carboxylic acid The amines of general formula II are all either commercially available products or are described in the literature.

b) When Z represents the —CO—NH— group, a compound of general formula II in which A represents —COOH or —COCl is condensed with a compound of general formula III in which B represents —NH$_2$. This reaction is carried out in the same manner as that described under a) above. The acids and acid chlorides of formula II and the amines of formula III are either commercially available or are described in the literature.

c) The compounds of formula I in which R$_4$ represents an optionally substituted benzyl group, acyl or alkyl substituted by alkanoyloxy, dialkylamino, alkoxy or phenoxy are prepared by reacting a compound of formula R$_4$X, R$_4$ being as previously defined and X representing a halogen, with a compound of formula I in which R$_4$ represents hydrogen.

d) The compounds of formula III as previously defined in which the heterocycle is an isoxazole (Y represents —O—) and R$_3$ represents the CHR$_{10}$OR$_5$ group, R$_5$ and R$_{10}$ being as previously defined and B represents the —COOH group, can be prepared
either by reacting a compound of formula

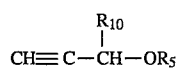

V

R$_5$ and R10 being as previously defined with a compound of formula:

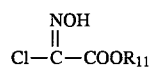

VI

R$_{11}$ representing a methyl or ethyl to produce a compound of formula:

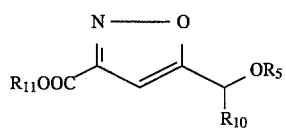

VII

R$_5$, R$_{10}$ and R$_{11}$ being as previously defined,
or by reacting a compound of formula:

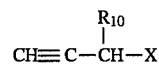

VIII

R$_{10}$ being as defined previously and X representing chlorine or bromine, with a compound of formula:

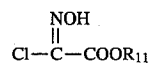

IX

R$_{11}$ being as defined previously, to produce a compound of formula:

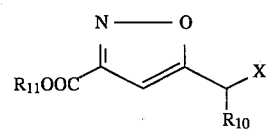

X

X being as defined above,
which is then reacted with an alcoholate of formula R$_5$—Na, R$_5$ being as previously defined, to produce a compound of formula X such as defined above, then the ester of formula X is hydrolysed to produce the corresponding acid of formula III.

Certain compounds of the invention possess one or more asymmetric carbon atoms. The corresponding optical isomers also form part of the invention.

More specifically the compounds of the formula Ia in which R$_4$ is C$_1$-C$_4$ alkyl may be prepared by condensing an acid chloride of the formula:

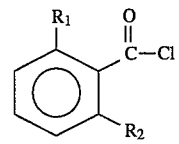

IIa with an amine of the formula:

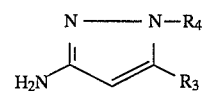

IIIa in the presence of a proton scavenger at a temperature of 20° to 120° C. in a solvent such as toluene, CH$_2$Cl$_2$, THF.

The compounds of the formula Ia in which R$_4$ is hydrogen may be obtained either:
by condensing an acid chloride of the formula IIa with an amine of the formula IIIa and separating the compounds from the N(pyrazolyl-5)benzamide or
by demethylating a compound of the formula Ia in which R$_4$ is methyl, by using pyridinium hydrochloride (D. E. Butler et al., J. Org. Chem., 40, 1975, 1815–22).

The compounds of the formula Ia in which R$_4$ is C$_2$-C$_7$ alkanoyl or hydroxymethyl may be obtained by condensing a compound of the formula Ia in which R4=H with either a corresponding acid chloride or HCHO.

The compounds of the formula Ia in which R$_3$ is hydroxymethyl may be obtained by hydrolysis of a compound of the formula Ia in which R$_3$=CH$_2$OCH$_2$—C$_6$H$_5$ by using boron trifluoride etherate (V. D. Vankar et al., J. Chem. Research, S-1985, 232). These latter compounds may be obtained by condensing an acid chloride of the formula IIa with an amine of the formula IIIa in which R$_3$=CH$_2$OCH$_2$—C$_6$H$_5$. This latter is obtained by condensing methylhydrazine on 4-benzyloxy buten-2-nitrile (adapted from R. E. Murray et al. Synthesis, 1980).

The following examples illustrate the preparation of the compounds of formula I.

EXAMPLE 1

Preparation of 3-(2,6-dimethyl phenylcarbamoyl) 1,5-dimethyl pyrazole (compound No. 4).

a) preparation of the ethyl ester of 1,5-dimethyl pyrazole 3-carboxylic acid 16.3 g (103.2 mmoles) of $CH_3$—CO—$CH_2$—CO—CO—O—$C_2H_5$ are introduced into a 250 ml round-bottomed flask. 5.5 ml (103.2 mmoles) of methylhydrazine are added dropwise and the mixture is heated at reflux for 2 hours. It is allowed to cool and the solvent is evaporated. The two isomers of the title are obtained by separating the mixture obtained by fractional distillation:

the ethyl ester of 1,5-dimethyl pyrazole 3-carboxylic acid: 9.85 g (yield 56.9%). B.p.: 92°–96° C./0.17 mmHg.

b) preparation of 1,5-dimethyl pyrazole 3-carboxylic acid.

To 9.8 g (58.3 mmoles) of the ethyl ester of 1,5-dimethyl pyrazole 3-carboxylic acid are added 50 ml of ethanol and 2.3 g (58.3 mmoles) of sodium hydroxide in 19.5 ml of water. 6.15 g of 1,5-dimethyl pyrazole 3-carboxylic acid are obtained in the form of colorless crystals (yield: 75.4%). M.p.=175° C.

c) preparation of 3-(2,6-dimethyl phenylcarbamoyl) 1,5-dimethyl pyrazole.

To 18.4 g (131.4 mmoles) of the compound obtained in the previous step, 11.3 ml (131.4 mmoles) of thionyl chloride are added in 1 l of toluene, followed by 15.9 g (131.4 mmoles) of 2,6-dimethyl aniline and 18 ml (131.4 ml) of triethylamine in 750 ml of toluene. 27.65 g of the title product are obtained in the form of ochre crystals.

Yield: 86.6%

M.p.=155° C.

EXAMPLE 2

Preparation of 3-(2,6-dimethyl phenylcarbamoyl) 5-methyl pyrazole (compound No. 1).

(D. E. Butler and H. A. Dewald JOC 1975, 40(9), 1353).

Into a 100 ml round-bottomed flask equipped with a condenser fitted with a $CaCl_2$ guard tube are introduced 5.8 g (40 mmoles) of pyridine hydrochloride and 2.4 g (10 mmoles) of the compound No. 4 obtained in the previous example. The mixture is heated at 220° C. for 12 hours. It is cooled, diluted with brine, extracted with ethyl acetate and dried over anhydrous $MgSO_4$. After evaporation of the solvent, purification by flash-chromatography and recrystallization from $CH_2Cl_2$ 0.4 g of the title product is obtained in the form of beige-coloured crystals.

Yield=21.2%

M.p.=198° C.

The compound of the title may also be obtained by proceeding in the following manner:

To 4 g (30 mmoles) of 5-methyl pyrazole 3-carboxylic acid are added 7.1 g (60 mmoles) of thionyl chloride, 150 ml of toluene and several drops of DMF. To the product obtained are then added 7.7 g of 2,6-dimethyl aniline (60 mmoles), 200 ml of toluene and again a few drops of DMF. 2.60 g of the title product are obtained in the form of ochre crystals.

Yield: 37.8%

M.p.=190° C.

EXAMPLE 3

Preparation of 3-(2,6-dimethyl phenylcarbamoyl) 1-methyl 5-methoxy pyrazole (compound No. 15) (according to S. Suguira; S. Ohno; 0. Ohtari; K. Iraini; T. Kitamikado; H. Asai; K. Kato; J. Med. Chem. 1977, 20, p. 80).

a) preparation of the ethyl ester of 1-methyl 5-methoxy pyrazole 3-carboxylic acid.

31 g (182 mmoles) of the ethyl ester of 1-methyl 5-hydroxy pyrazole 3-carboxylic acid, 22.9 g (182 mmoles) of dimethyl sulfate, 12.5 g (91 mmoles) of $K_2CO_3$ and 500 ml of acetone are introduced into a 1 liter round-bottomed flask. The mixture is heated at reflux for 5 hours.

It is allowed to cool, the precipitate obtained is filtered off, the solvent is evaporated, the residue is taken up in acetone and the precipitate obtained is filtered off. 12 g of colorless crystals are obtained (M.p.: 78° C.). The filtrate still contains 19 g of impure product (yield: 90%).

b) preparation of 1-methyl 5-methoxy pyrazole 3-carboxylic acid.

To 12 g (65.2 mmoles) of the ester obtained in the previous step are added 100 ml of ethanol and 2.6 g (62.5 mmoles) of sodium hydroxide in 50 ml of water. The mixture is left overnight at room temperature. 9 g of the acid are obtained.

Yield: 88.5%

M.p. =194° C.

c) preparation of 3-(2,6-dimethyl phenylcarbamoyl) 1-methyl 5-methoxy pyrazole.

To 9 g (57.6 mmoles) of the product obtained in the previous step are added 200 ml of toluene and 6.86 g (57.6 mmoles) of thionyl chloride. The mixture is heated at reflux for 6 hours. 10.5 g of the acid chloride are obtained (M.p. =76° C.).

To the acid chloride obtained are added 7.28 g (60.1 mmoles) of dimethylaniline, 6.07 g (60.1 mmoles) of triethylamine and 200 g of toluene. 11 g of the title product are obtained in the form of colorless crystals.

Yield: 73.7%

M.p. =144° C.

EXAMPLE 4

Preparation of 3-(2,6-dimethyl phenylcarbamoyl) 1-benzyl 5-methyl pyrazole (compound No. 14).

The substance is prepared as described by G. Tarrago and A. Ramdari (J. Hetero Chem. 17, 137 (1980)).

In a 100 ml round-bottomed flask equipped with a condenser fitted with a $CaCl_2$ guard tube are introduced 1 g (4.4 mmoles) of compound No. 1 obtained in example No. 2. 30 ml of DMF, 7.50 mg (4.4 mmoles) of benzyl bromide and 2.1 g (13 mmoles) of potassium iodide are added. The mixture is heated for 1 h at 100° C. After evaporation of the solvent, the residue is taken up in chloroform. The organic phase is washed with a solution of sodium thiosulfate then with water and is dried over $Na_2SO_4$.

After evaporation of the solvent and purification by flash chromatography 0.2 g of the title product is obtained in the form of colorless crystals.

Yield: 14.3%

M.p. =147° C.

EXAMPLE 5

Preparation of 3-(2,6-dimethyl phenylcarbamoyl) 5-methoxymethyl isoxazole (compound No. 21).

a) preparation of the ethyl ester of 5-methoxymethyl isoxazole 3-carboxylic acid.

9 g (0.128 mmole) of methoxypropargyl ether prepared according to L. A. CABE, D. R. BENEDICT, T. A. BIANCHI (Synthesis, 428, 1979) are added to 100 ml of chloroform. 69 g of $K_2CO_3$ (0.5 mole) are added at room temperature and the mixture obtained is stirred mechanically at this temperature.

19.5 g (0.129 mole) of ethyl chlorooximidoacetate are then added dropwise (J. ORG. CHEM., 48(3), 371, 1983).

When the reaction is complete, the reaction mixture is rinsed with 50 ml of $CHCl_3$ and stirred for 48 hours. The $K_2CO_3$ is filtered off, the chloroform is evaporated and the product is purified by distillation. 13 g of pure product are obtained.

Yield : 59%

$B.p._{20}=168°-172°$ C.

b) preparation of 5-methoxymethyl isoxazole 3-carboxylic acid 13 g (0.075 mole) of the product obtained in the previous step are suspended in 40 ml of water. The mixture is cooled in an ice bath. 12 ml (0.120 mole) of a 30% sodium hydroxide solution are then added. The temperature is allowed to rise to room temperature and the mixture is stirred for 1 hour. The reaction mixture is cooled again and 12 ml of 37% HCl are added. The water is evaporated, the residue is taken up in acetone, the solution is filtered, dried over $MgSO_4$ and the solvent is evaporated.

c) preparation of 3-(2,6-dimethyl phenylcarbamoyl) 5-methoxymethyl isoxazole.

The procedure used is that described in J. MED. CHEM., 30(11), 2008–2012.

4.3 g of 2,6-dimethylaniline (0.036 mole) are added to 100 ml of THF and cooled in an ice-water bath. 4.2 ml (0.045 mole) of $POCl_3$ are added, followed by 7 g (0.045 mole) of the product obtained in the previous step. The mixture is left to stand for ½ hour. 9 ml of triethylamine in 50 ml of THF are added slowly. The mixture is slowly allowed to attain room temperature and is stirred overnight.

It is extracted with ethyl acetate, washed with a saturated NaCl solution to neutral pH, dried over $MgSO_4$ and the solvent is evaporated. The crude product obtained is purified on a column of silica (eluent $CH_2Cl_2$). 4.3 g of the title product are obtained.

Yield: 46%.

EXAMPLE 6

Preparation of 3-(2,6-dimethyl phenylcarbamoyl) 5-(2,6-dimethoxy phenoxymethyl) isoxazole (compound No. 25).

a) preparation of the methyl ester of 5-(2,6-dimethoxy phenoxymethyl) isoxazole 3-carboxylic acid.

5.1 g (0.023 mole) of the methyl ester of 5-bromomethyl isoxazole 3-carboxylic acid, 3.6 g of 2,6-dimethoxy phenol (0.023 mole) and 5 g of $K_2CO_3$ (0.036 mole) in 150 ml of acetone are heated at reflux for 6 hours.

The $K_2CO_3$ is filtered off, rinsed with acetone and the solvent is evaporated.

6.2 g of pure product are obtained (yield: 100%).

b) preparation of 5-(2,6-dimethoxy phenoxymethyl) isoxazole 3-carboxylic acid.

6.7 g of the ester obtained in the previous step are dissolved in 200 ml of methanol. 1.5 g of sodium hydroxide (0.0375 mole) in 20 ml of water are added and the mixture is stirred at room temperature until all trace of the ester has disappeared. The solvent is then evaporated. The sodium salt is dissolved in water, acidified in the cold to pH2 to precipitate the acid. It is filtered off and dried over $P_2O_5$. 6.5 g of the title product are thus obtained.

Yield: 100%.

c) preparation of 3-(2,6-dimethyl phenylcarbamoyl) 5-(2,6-dimethoxy phenoxymethyl) isoxazole.

6.5 g of the product obtained in the previous step and 2.9 g of 2,6-dimethylaniline (0.023 mole) are added to 150 ml of THF and the solution is cooled to 0° C.

2.8 ml (0.030 mole) of $POCl_3$ are added. The mixture is left for ½ hour. 7 ml (0.070 mole) of triethylamine in 50 ml of THF are then added slowly. The mixture is left to stand for 12 hours, filtered through a fritted glass filter and the solvent is evaporated.

The crude product obtained is purified on a column of silica (eluent: $CH_2Cl_2$)

4.6 g of product are obtained.

Yield: 50%.

EXAMPLE 7

Preparation of 3-(2,6-dimethyl phenylcarbamoyl) 5-acetoxy methyl isoxazole (compound No. 27).

a) preparation of the methyl ester of 5-hydroxymethyl isoxazole 3-carboxylic acid 60 g (0.436 mole) of methyl chlorooximidoacetate in 100 ml of chloroform are added very slowly to a solution composed of 30 g (0.535 mole) of propargyl alcohol and 180 g (1.3 mole) of $K_2CO_3$ in 50 ml of chloroform.

The addition is accompanied by an exothermic reaction which causes the chloroform to reflux.

After being allowed to cool to room temperature, the mixture is stirred for 6 hours.

Thin layer chromatography (eluent: $CH_2Cl_2$/MeOH: 98/2) shows the degree of conversion to be 100%.

The reaction mixture is filtered through a fritted glass filter, the residue is rinsed with chloroform and the solvent evaporated under reduced pressure.

The crude title product is obtained in a purity of about 100%.

b) preparation of 5-hydroxymethyl isoxazole 3-carboxylic acid.

38 g (0.242 mole) of the product obtained in the previous step are suspended in 50 ml of distilled water.

After the suspension has been cooled in an icebath 10 g (0.25 mole) of sodium hydroxide in 50 ml of distilled water are added dropwise.

The reaction mixture is stirred at 0° C. for 1 hour, then for 1 hour at room temperature.

The mixture is cooled again to 0° C., the sodium hydroxide in excess is neutralized with dilute HCl followed by acidification to pH2.

The water is evaporated, the residue is taken up in acetone, the insoluble NaCl is filtered off, the filtrate is dried over $MgSO_4$ and the solvent is evaporated.

c) preparation of 5-acetoxymethyl isoxazole 3-carboxylic acid.

25 g (0.16 mole) of the product obtained in the previous step are suspended in a mixture composed of 125 ml of acetic anhydride and 25 ml of glacial acetic acid.

5 drops of $H_2SO_4$ are added and, when the starting materials have completely dissolved, the reaction mixture is heated for 1 hour at 60° C.

Thin layer chromatography (eluent: $CH_2Cl_2$/MeOH: 80/20) shows that the reaction is complete at this stage.

The acetic acid and acetic anhydride are removed by distillation under reduced pressure.

29 g of the title product are obtained.

Yield: 98%

M.p.=84° C.

d) preparation of 3-(2,6-dimethyl phenylcarbamoyl) 5-acetoxymethyl isoxazole.

20 g (0.16 mole) of 2,6-dimethyl aniline are added to 200 ml of anhydrous THF and cooled to 0° C. in an icebath.

18.5 ml (0.20 mole) of $POCl_3$ are added slowly, followed by 29 g (0.16 mole) of the product obtained in the previous step diluted in 150 ml of dry THF.

50 ml of triethylamine in 50 ml of dry THF are then added very slowly.

The mixture is stirred continuously at room temperature for 12 hours.

The triethylamine hydrochloride is filtered off and the reaction mixture washed by means of acetone.

After evaporation of the solvents, the crude product obtained is purified on a column of silica (eluent: $CH_2Cl_2$).

46 g of the title product are obtained.

Yield: 100%.

EXAMPLE 8

Preparation of 3-(2,6-dimethyl phenylcarbamoyl) 5-t-butyryloxymethyl isoxazole (compound No. 28).

a) preparation of 3-(2,6-dimethyl phenylcarbamoyl) 5-hydroxymethyl isoxazole.

(according to J. Med. Chem., 32(8), 1868, 1989).

14 g (0.0486 mole) obtained in the previous example are dissolved in 50 ml of methanol and cooled to 5° C. in an ice-water bath.

4.5 ml of a 28% solution of ammonia are added and the mixture is stirred at room temperature for 12 hours.

After evaporation of the solvent, the crude product is purified on a column of silica (eluent: gradient $CH_2Cl_2$—$CH_2Cl_2$/MeOH: 97/3).

9 g of the pure title product are obtained.

Yield: 76%

M.p. =100° C.

b) preparation of 3-(2,6-dimethyl phenylcarbamoyl) 5-t-butyryloxymethyl isoxazole.

5 g (0.020 mole) of the product obtained in the previous step are dissolved in 150 ml of THF and the solution is cooled in an ice-water bath.

7 ml (0.070 mole) of triethylamine are added in one portion, followed by the dropwise addition of 2.6 ml (0.020 mole) of pivaloyl chloride in 50 ml of THF with vigorous stirring. The mixture is allowed to attain room temperature, is stirred for 12 hours, filtered through a fritted glass filter, the solvent is evaporated and the crude product obtained is purified on a column of silica (eluent: acetone).

5.5 g of the title product are obtained.

Yield: 85%.

EXAMPLE 9

Preparation of N-(1,5-dimethylpyrazol-3-yl)-2,6 dimethyl benzamide (compound 3)

To a cooled (0°–5° C.) solution of 3-amino-1,5-dimethyl pyrazole (95%, 32.7 g, 0.28M) in anhydrous $CH_2Cl_2$ (200 ml) was added a $CH_2Cl_2$ (100 ml) solution of the 2,6 dimethyl benzoyl chloride (23.6 g, 0.14M). The reaction mixture was allowed to room temperature for 18 hours and then $CH_2Cl_2$ was concentrated to give an oily mixture which was diluted in AcOEt. This suspension was then treated with saturated $NaHCO_3$. After usual work-up, the crude material was cristallized with diisopropyloxide to give 13 g of the desired amide (38% : yield based on the 2,6-dimethyl benzoyl chloride).

m.p.: 184° C.

EXAMPLE 10

Preparation of N-(5-methylpyrazol-3-yl)-2,6,dimethyl benzamide (compound 42)

To a cooled (10° C.) solution of 3-amino-5-methyl pyrazole (98%, 9.9 g; 0.1M) and triethylamine (99%, 10.2 g; 0.1M) in anhydrous $CHCl_3$ (75 ml) under nitrogen atmosphere was added dropwise 2,6-dimethyl benzoyl chloride (17.0 g; 0.1M) in $CHCl_3$ (25 ml). The temperature rose to 20°–5° C. After 3 hours at room temperature, the mixture was then heated for 2 hours at 50° C. and allowed to R.T., then diluted with $CHCl_3$ (200 ml) and poured onto ice water (100 g) under vigourous agitation. The organic layer was washed with saturated $NaHCO_3$ (2×25 ml) and dried with $MgSO_4$.

The crude material was purified by column chromatography on silica gel (60–200 microns) using $CH_2Cl_2$ and $CH_2Cl_2/CH_3OH$=97.5/2.5 and 95/5 (v/v) as eluents. After separation the 2,6 dimethyl benzoyl anhydride, 3 amides were separated successively to give N-(3-methylpyrazol-5-yl)-2,6 dimethyl benzamide (compound 42a)(13%), 3(5)-amino-5(3)-methyl-N1-(2,6-dimethyl benzoyl) pyrazole (compound 42b)(6.5%) and N-(5-methylpyrazol-3-yl)-2,6 dimethyl benzamide (compound 42) (24%) (Total yield 43.5 %).

m.p. of 42: 252° C.

m.p. of 42a: 204° C.

m.p. of 42c: 128° C.

EXAMPLE 11

Preparation of N-(5-methylpyrazol-3-yl)-2,6 dimethyl benzamide (compound 42) by demethylation.

The compound 3 (7.0 g; 29 mM) was added to anhydrous pyridinium hydrochloride (15 fold molar exces) and the mixture was heated at 220° C. for 2 hours to give after usual work-up (dilution the solution with 50 g of ice water, treatment with aqueous $NaHCO_3$ and extraction with $CHCl_3$ (100 ml), the crude material which was purified by column chromatography on silica gel (60–200 microns) using $CH_2Cl_2$ and $CH_2Cl_2/CH_3OH$=97.5/2.5, as eluents giving 1.5 g (22%) of the demethylated compound and 3 g of the recovered amide.

m.p.: 252° C.

EXAMPLE 12

Preparation of N-(1-acetyl-5-methylpyrazol-3-yl )-2, 6 dimethyl benzamide (compound 10).

To a cooled (−3/0° C.) solution of the compound 42 (2.3 g; 0.01M) and pyridine (0.8 g; 0.01M) in anhydrous $CH_2Cl_2$ (30 ml) under nitrogen atmosphere was added dropwise a solution of acetyl chloride (0.8 g; 0,01M) in $CH_2Cl_2$ (10 ml ) over 10 minutes. The mixture was allowed to room temperature for 1 hour and poured onto ice water and $CH_2Cl_2$ (50 ml ), washed with saturated $NaHCO_3$ and dried with $MgSO_4$. The crude product was cristallized with pentane to give 1.7 g of the corresponding N1-acetyl amide.

Yield: 63% m.p.: 152° C.

EXAMPLE 13

Preparation of N-(5-hydroxymethyl-1-methylpyrazol-3-yl)-2,6-dimethyl benzamide (compound 43).

a) Preparation of 3-amino-5-benzyloxymethyl-1-methyl pyrazole

To a cooled (–5°/0° C.) solution of 4-benzyloxybuten-2-nitrile (42.8 g; 0.25M) (adapted from R. E. Murray & G. Zweifel, Synthesis 1980 (2), 150-1) in anhydrous EtOH.(200 ml) was added anhydrous methyl hydrazine (13.8 g; 0.3M) in EtOH (50 ml) over 30 mn.

The mixture was allowed to room temperature for 90 mn, then slowly poured onto cold HCl (37%, 60 g) diluted with of ice water (100 g) over 15 mn.

The reaction mixture was then treated with cold 30% NaOH (80 g).

EtOH was distillated under vacuo and the crude residue was extracted with AcOEt. After usual work-up, the crude material was chromatographied on silica gel (60–200 microns, 400 g) using. $CH_2Cl_2$, $CH_2Cl_2/CH_3OH=95/5$ and 9/1 l(v/v) as eluents to give an oil (21.5 g, 40%) which was a mixture of the 3-amino-5-benzyloxymethyl-1-methyl pyrazole and its 5-amino-3-benzyloxymethyl isomer in the approximated ratio of 3/1 ($^{1H}$NMR).

$^{1H}$NMR ($CDCl_3$) ppm for the 3-amino-isomer: 3.25 (2H, br, $NH_2$), 3.64 (3H, s, N—$CH_3$), 4.39 (2H, s, $CH_2$—O), 4.48 (2H, s, O—$CH_2$—Ar), 7.30 (5H, m, $C_6H_5$ ).

$^{1H}$NMR ($CDCl_3$) ppm for the 5-amino-isomer: 3.25 (2H, br, $NH_2$), 3.58 (3H, s, N—$CH_3$), 4.41 (2H, s, $CH_2O$), 4.53 (2H, s, O—$CH_2$—Ar), 7.30 (5H, m, $C_6H_5$).

b) preparation of N-(5-hydroxymethyl-1-methylpyrazol-3-yl)-2,6-dimethyl benzamide (compound 43).

To a cooled (0° C.) suspension of N-(1-methyl-5 -benzyloxymethylpyrazol-3-yl)-2,6-dimethyl benzamide (9 g, 0.025M) and sodium iodide (19 g, 0.125M) in acetonitrile (250 ml) was added boron trifluoride etherate (18,3 g, 0,125M) in acetonitrile (60 ml) under nitrogen atmosphere. After being stirred for 2 hours at room temperature and usual work-up, the crude material was purified by column chromatography on silica gel using $CH_2Cl_2$, then $CH_2Cl_2/CH_3OH=97.5/2.5$ and 95/5 as eluents to give 1.5 g (23%) of a white solid.

m.p.: 214° C.

The compounds of these examples as well as the other compounds of formula I are presented in Table II below. The compounds according to the invention have been found to possess properties which exert useful effects on the central nervous system in particular anti-convulsant properties likely to make them useful in the treatment of epilepsy or as a supplement to anticonvulsant therapy, and properties of cerebral protection and memory enhancement.

Thus, the invention also includes the therapeutic compositions containing the compounds of the general formula I as active ingredients.

The pharmacological and toxicological results demonstrating the properties of the compounds of formula I will be given below.

Pharmacological activity

1. Materials and methods 1.1 Animals

Male mice CD1 (Charles River, France) in the weight range 22–28 g were used. The animals were housed at a constant room temperature (22°±2° C.) and relative humidity (50%) with a 12 h light/12 h dark cycle (light off at 7.00 pm) with food and tap water continuously available.

1.2 Compound

The tested compound suspended in a 1% aqueous solution of Tween 80 was administered intraperitoneally (ip) in a volume of 0.1 ml/10 g body weight. The dosage levels (at least three different doses) were selected following the IRWIN test investigation.

1.3 Neurotoxicity (IRWIN test)

The neurologic and behaviour symptomatology was observed during 3 hours after the ip administration of the tested compound. The dosage inducing a neurotoxicity in 3/5 of the animals was estimated.

1.4 Maximal electroshock seizure (MES) test

Maximal seizure were induced 30 min after drug treatment by application of an electric current across the brain via corneal electrodes.

The stimulus parameters were pulses of 50 Hz and 50 mA for 0.2 sec. The abolition of the hind limb tonic extensor component of maximal seizure was defined as protection.

1.5 Pentylenetetrazole seizure (PTZ) test 70 mg/kg of pentylenetetrazole were injected as a 1% solution subcutaneously 30 min ip after injection of the test compound. Failure to observe convulsions was defined as protection.

1.6 ED50

The parallel line assay of FINNEY was used to estimate the ED50 value and the 95% confidence limits with the aid of a computer.

The results are given in Table I.

TABLE I

| | Quantitative anticonvulsant activity in mice (ip route) | | |
|---|---|---|---|
| Compound | Neurotoxicity/IRWIN mg/kg | Electroshock ED50 mg/kg | Pentetrazole ED50 mg/kg |
| 3 | <100 | 39(28–54) | 27(16–46) |
| 8 | >100 | 100 | 100 |
| 10 | >100 | >100 | >100 |
| 42 | <100 | 25(16–39) | 38(25–28) |
| 43 | >100 | >100 | >100 |
| 44 | 100 | 24(17–34) | 35(22–53) |
| 45 | 100 | <75 | 75 |

The therapeutic compositions according to the invention may be administered by the oral, parenteral or rectal routes.

They may be in the form of tablets, sugar-coated pills, capsules, injectable solutions or suspensions and suppositories.

The amount of the active ingredient administered obviously depends on the patient who is being treated, the route of administration and the severity of the disease.

However, the daily dose should be of the order of 10 to 300 mg.

The unit dose may vary from 10 to 100 mg.

EXAMPLES OF FORMULATION

1) Tablet-type formula:

| For 5000 20 mg tablets | |
|---|---|
| Compound of example 2 | 100 g |
| Microcrystalline cellulose | 1000 g |
| Carboxymethyl cellulose sodium | 15 g |
| Magnesium stearate | 10 g |
| Total | = 1125 g |

Mix all of the constituents in a Turbula® mixer for 10 min.

Compression on an alternative machine, theoretical weight: 225 mg.

2) Capsule-type formulae:

| For 5000 size 1 capsules containing a 10 mg dose | |
|---|---|
| Compound of example 2 | 50 g |
| Mais starch | 150 g |
| Lactose | 1250 g |
| PVP K30 | 75 g |
| Talc | 30 g |
| Magnesium stearate | 10 g |
| Total | = 1565 g |

-continued

| For 5000 size 1 capsules containing a 10 mg dose | |
|---|---|
| 50° alcohol | = QS |

Mix the following constituents for 10 min. in a planetary mixer: compound No. 1 -mais starch-lactose-PVP.

Continue the mixing and pour in the alcohol slowly until granulation is sufficient.

Spread on trays, dry in an oven at 50° C.

Calibrate on an oscillating granulator, using a 1 mm grid.

Mix the grain with the talc and the magnesium stearate for 10 min in the Turbula®.

Place in capsules, theoretical weight: 313 mg.

TABLE II

Examples of compounds of the invention

| Compound No. | ![N-Y structure with R3] | Z | $R_1$ | $R_2$ | M.p. (°C.) |
|---|---|---|---|---|---|
| 1 | N——N—H, CH₃ | —NH—CO— | $CH_3$ | $CH_3$ | 190 |
| 2 | N——N—COCH₃, CH₃ | —NH—CO— | $CH_3$ | $CH_3$ | 151 |
| 3 | N——N(CH₃), CH₃ | —CO—NH— | $CH_3$ | $CH_3$ | 186 |
| 4 | N——N(CH₃), CH₃ | —NH—CO— | $CH_3$ | $CH_3$ | 144 |
| 5 | N——N(CH₃), CH₃ | —NH—CO— | $CH_3$ | Cl | 182 |
| 6 | N——N(CH₃), CH₃ | —NH—CO— | $C_3H_7$-iso | $CH_3$ | 100 |
| 7 | N——N(CH₃), CH₃ | —N(CH₃)—CO— | $CH_3$ | $CH_3$ | 134 |
| 8 | N——N(CH₃), OCH₃ | —CO—NH— | $CH_3$ | $CH_3$ | 157 |
| 9 | N——N(CH₃), CH₃ | —NH—CO—CH=CH— | $CH_3$ | $CH_3$ | 112 |

TABLE II-continued

Examples of compounds of the invention

| Compound No. | (N—Y structure with R₃) | Z | R₁ | R₂ | M.p. (°C.) |
|---|---|---|---|---|---|
| 10 | N—N(COCH₃), CH₃, CH₃ | —CO—NH— | CH₃ | CH₃ | 154 |
| 11 | N—O, CH₂OH | —CO—NH— | CH₃ | CH₃ | 132 |
| 14 | N—N(CH₂-phenyl), CH₃ | —NH—CO— | CH₃ | CH₃ | 147 |
| 15 | N—N(CH₃), OCH₃ | —NH—CO— | CH₃ | CH₃ | 134 |
| 16 | N—O, CH(OH)CH₃ | —NH—CO— | CH₃ | CH₃ | huile |
| 18 | N—O, CH₂OCONH₂ | —NH—CO— | CH₃ | CH₃ | 135 |
| 20 | N—O, COCH₃ | —NH—CO— | CH₃ | CH₃ | 117 |
| 21 | N—O, CH₂OCH₃ | —NH—CO— | CH₃ | CH₃ | 87 |
| 22 | N—O, CH₂O-phenyl | —NH—CO— | CH₃ | CH₃ | 116 |
| 23 | N—O, CH₂O-(4-Br-phenyl) | —NH—CO— | CH₃ | CH₃ | 99 |
| 24 | N—O, CH₂O-(4-F-phenyl) | —NH—CO— | CH₃ | CH₃ | 107 |
| 25 | N—O, CH₂O-(2,6-diOCH₃-phenyl) | —NH—CO— | CH₃ | CH₃ | 75 |

5,464,860

TABLE II-continued

Examples of compounds of the invention

| Compound No. | [N—Y / R3 structure] | Z | R1 | R2 | M.p. (°C.) |
|---|---|---|---|---|---|
| 26 | isoxazole with -CH2-O-C6H4-CF3 (meta) | —NH—CO— | CH3 | CH3 | 118 |
| 27 | isoxazole with -CH2-O-C(=O)-CH3 | —NH—CO— | CH3 | CH3 | 71 |
| 28 | isoxazole with -CH2-O-C(=O)-C4H9-tert | —NH—CO— | CH3 | CH3 | 132 |
| 29 | isoxazole with -CH2-O-C(=O)-phenyl | —NH—CO— | CH3 | CH3 | 69 |
| 30 | isoxazole with -CH2-O-C(=O)-N(CH3)2 | —NH—CO— | CH3 | CH3 | 82 |
| 17 | isoxazole with CH3 | —CO—NH— | CH3 | CH3 | 180 |
| 31 | isoxazole with -CH2F | —NH—CO— | CH3 | CH3 | 90 |
| 32 | isoxazole with -CH2Cl | —NH—CO— | CH3 | CH3 | 130 |
| 33 | pyrazole with -(CH2)3-O-C6H4-F (para) and CH3 | —NH—CO— | CH3 | Cl | 157 |
| 34 | pyrazole with N-COCH3 and OCH3 | —NH—CO— | CH3 | Cl | 192 |
| 35 | pyrazole with N-CH2CH2-OCH3 and CH3 | —NH—CO— | CH3 | Cl | 97 |

TABLE II-continued

Examples of compounds of the invention

| Compound No. | (structure with N—Y / R₃) | Z | $R_1$ | $R_2$ | M.p. (°C.) |
|---|---|---|---|---|---|
| 36 | N—N—CH₂—C₆H₅ ; OCH₃ | —NH—CO— | $CH_3$ | Cl | 97 |
| 37 | N—N—CH₂CH₂—O—C(O)CH₃ ; CH₃ | —NH—CO— | $CH_3$ | Cl | 113 |
| 38 | N—N—CH₂CH₂N(C₂H₅)₂ ; CH₃ | —NH—CO— | $CH_3$ | Cl | 66 |
| 39 | N—N—CH₃ ; O—CH₂CH₂N(C₂H₅)₂ | —NH—CO— | $CH_3$ | Cl | 71 |
| 40 | N—N—CH₂CH₂OCH₃ ; OCH₃ | —NH—CO— | $CH_3$ | Cl | 97 |
| 41 | N—N—COCH₃ ; CH₃ | —NH—CO— | $CH_3$ | $CH_3$ | 181 |
| 42 | N—N—H ; CH₃ | —CO—NH— | $CH_3$ | $CH_3$ | 252 |
| 43 | N—N—CH₃ ; CH₂OH | —CO—NH— | $CH_3$ | $CH_3$ | 213 |
| 44 | N—N—CH₂OH ; CH₃ | —CO—NH— | $CH_3$ | $CH_3$ | 150/240 |
| 45 | N—N—CH₃ | —CO—NH— | $CH_3$ | $CH_3$ | 149 |

We claim:

1. A compound selected from the compounds of the general formula:

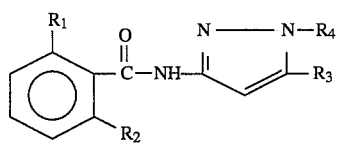

Ia in which
  $R_1$ is $C_1$–$C_4$ alkyl,
  $R_2$ is $C_1$–$C_4$ alkyl,
  $R_3$ is selected from hydrogen, $C_1$–$C_4$ alkyl, $C_1$–$C_4$ alkoxy and $C_1$–$C_4$ hydroxyalkyl, and
  $R_4$ is selected from hydrogen, $C_1$–$C_4$ alkyl, $C_2$–$C_7$ alkanoyl and $C_1$–$C_4$ hydroxyalkyl.

2. A compound as claimed in claim 1, in which $R_4$ is selected from hydrogen, methyl, hydroxymethyl and acetyl.

3. A compound as claimed in claim 1 in which $R_3$ is selected from hydrogen, methyl, methoxy and hydroxymethyl.

4. A heterocyclic compound as claimed in claim 1, in which $R_1$ and $R_2$ are methyl.

5. N-(1,5-dimethyl pyrazol-3-yl)-2,6-dimethyl benzamide.

6. N-(5-methyl pyrazol-3-yl)-2,6-dimethylbenzamide.

7. A pharmaceutical composition useful in treating epilepsy, which contains a pharmaceutically effective amount of a compound according to claim 1 and a carrier or excipient.

8. A pharmaceutical composition useful in treating epilepsy, which contains a pharmaceutical effective amount of the compound of claim 5 and an excipient or carrier.

9. A pharmaceutical composition useful in treating epilepsy, which contains a pharmaceutical effective amount of the compound of claim 6 and an excipient or carrier.

10. A method for treating epilepsy in a patient, which comprises administering to said patient a therapeutically effective amount of a compound of claim 1.

* * * * *